United States Patent
Massicotte et al.

(10) Patent No.: US 8,529,581 B2
(45) Date of Patent: *Sep. 10, 2013

(54) METHOD AND DEVICE FOR EXTRACTING OBJECTS FROM THE BODY

(71) Applicants: J. Mathieu Massicotte, North Reading, MA (US); Peter J. Massicott, Boston, MA (US)

(72) Inventors: J. Mathieu Massicotte, North Reading, MA (US); Peter J. Massicott, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/693,613

(22) Filed: Dec. 4, 2012

(65) Prior Publication Data
US 2013/0096571 A1   Apr. 18, 2013

Related U.S. Application Data

(63) Continuation of application No. 11/503,617, filed on Aug. 14, 2006, now Pat. No. 8,343,170.

(60) Provisional application No. 60/708,124, filed on Aug. 12, 2005.

(51) Int. Cl.
*A61B 17/22* (2006.01)

(52) U.S. Cl.
USPC ........................................................ 606/127

(58) Field of Classification Search
USPC .......... 604/102.02, 103.08, 103.14; 606/110, 606/127, 128, 192
See application file for complete search history.

(56) References Cited

U.S. PATENT DOCUMENTS

| | | | |
|---|---|---|---|
| 3,746,003 A * | 7/1973 | Blake et al. | 604/102.02 |
| 4,243,040 A | 1/1981 | Beecher | |
| 4,295,464 A | 10/1981 | Shihata | |
| 4,324,262 A * | 4/1982 | Hall | 600/569 |
| 4,469,100 A | 9/1984 | Hardwick | |
| 4,820,270 A * | 4/1989 | Hardcastle et al. | 604/96.01 |
| 4,927,426 A | 5/1990 | Dretler | |
| 4,946,440 A * | 8/1990 | Hall | 604/164.09 |
| 5,300,023 A * | 4/1994 | Lowery et al. | 604/515 |
| 5,374,247 A * | 12/1994 | Lowery et al. | 604/515 |
| 6,218,016 B1 | 4/2001 | Tedeschi et al. | |
| 6,692,484 B1 | 2/2004 | Karpiel et al. | |
| 8,343,170 B2 * | 1/2013 | Massicotte et al. | 606/127 |
| 2004/0015182 A1* | 1/2004 | Kieturakis et al. | 606/190 |
| 2004/0059290 A1 | 3/2004 | Palasis | |
| 2007/0173785 A1* | 7/2007 | Ostroot | 604/509 |

FOREIGN PATENT DOCUMENTS

| | | |
|---|---|---|
| EP | 0200668 | 11/1986 |
| WO | 2005102184 | 11/2005 |

OTHER PUBLICATIONS

The International Search Report and the Written Opinion issued in connection with PCT Application No. PCT/US2006/031583 mailed on Dec. 28, 2006.

* cited by examiner

*Primary Examiner* — Ryan Severson
*Assistant Examiner* — Jonathan W Miles
(74) *Attorney, Agent, or Firm* — Gesmer Updegrove LLP

(57) ABSTRACT

A device for extracting (or inserting) objects from the body, such as urinary stones, using a low pressure inflatable toroidal balloon that serves to engulf the object during extraction (or insertion) while dilating and protecting the passageway. The balloon loads onto an ureteroscope prior to insertion, rather than through the ureteroscope as do existing balloons. The toroidal balloon is a simple and unique device that may be applied external to the extracting telescope and does not interfere with existing methods for stone manipulation such as laser lithotripsy, irrigation and basket extraction in the case of urinary stone manipulation.

14 Claims, 12 Drawing Sheets

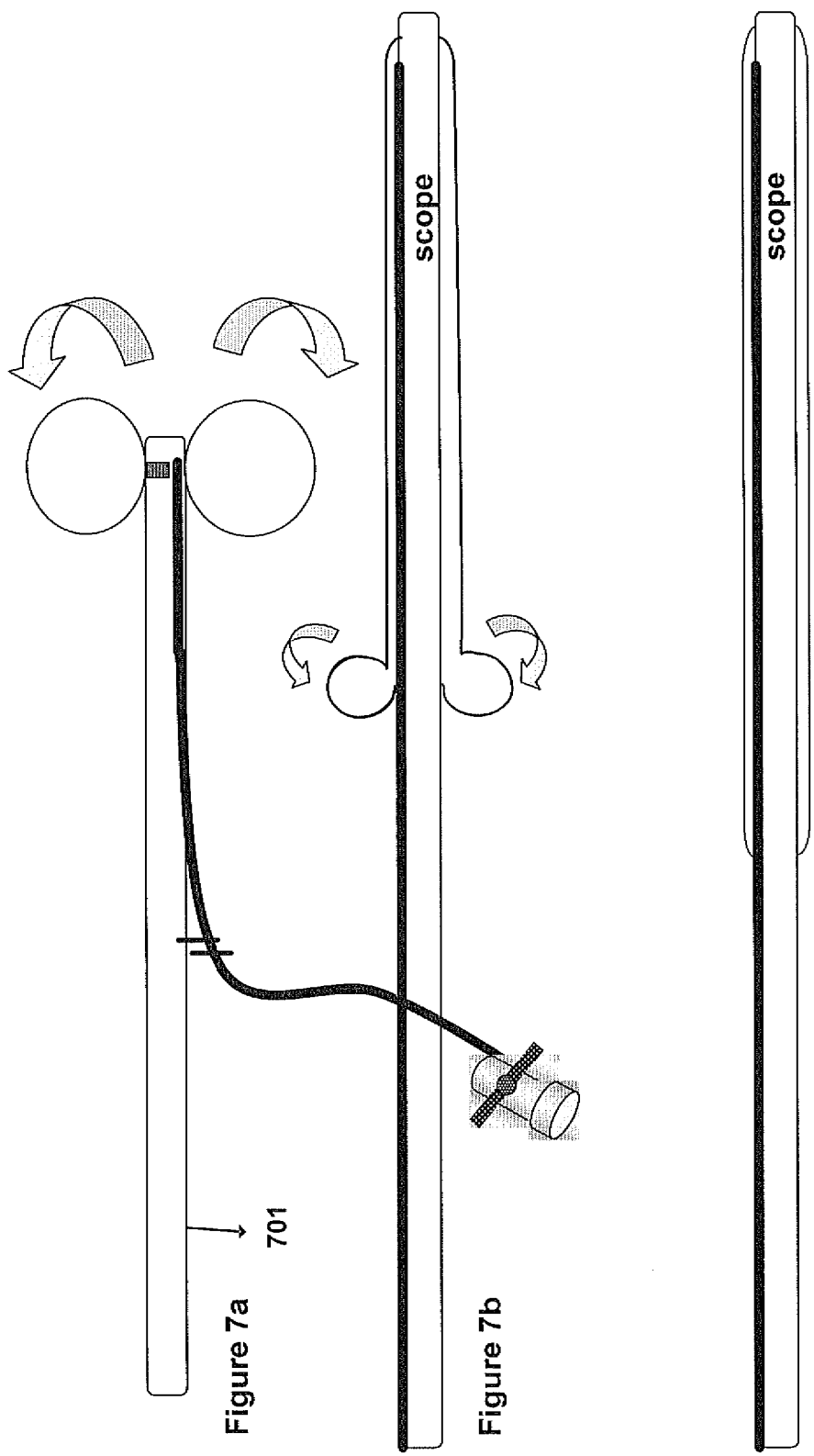

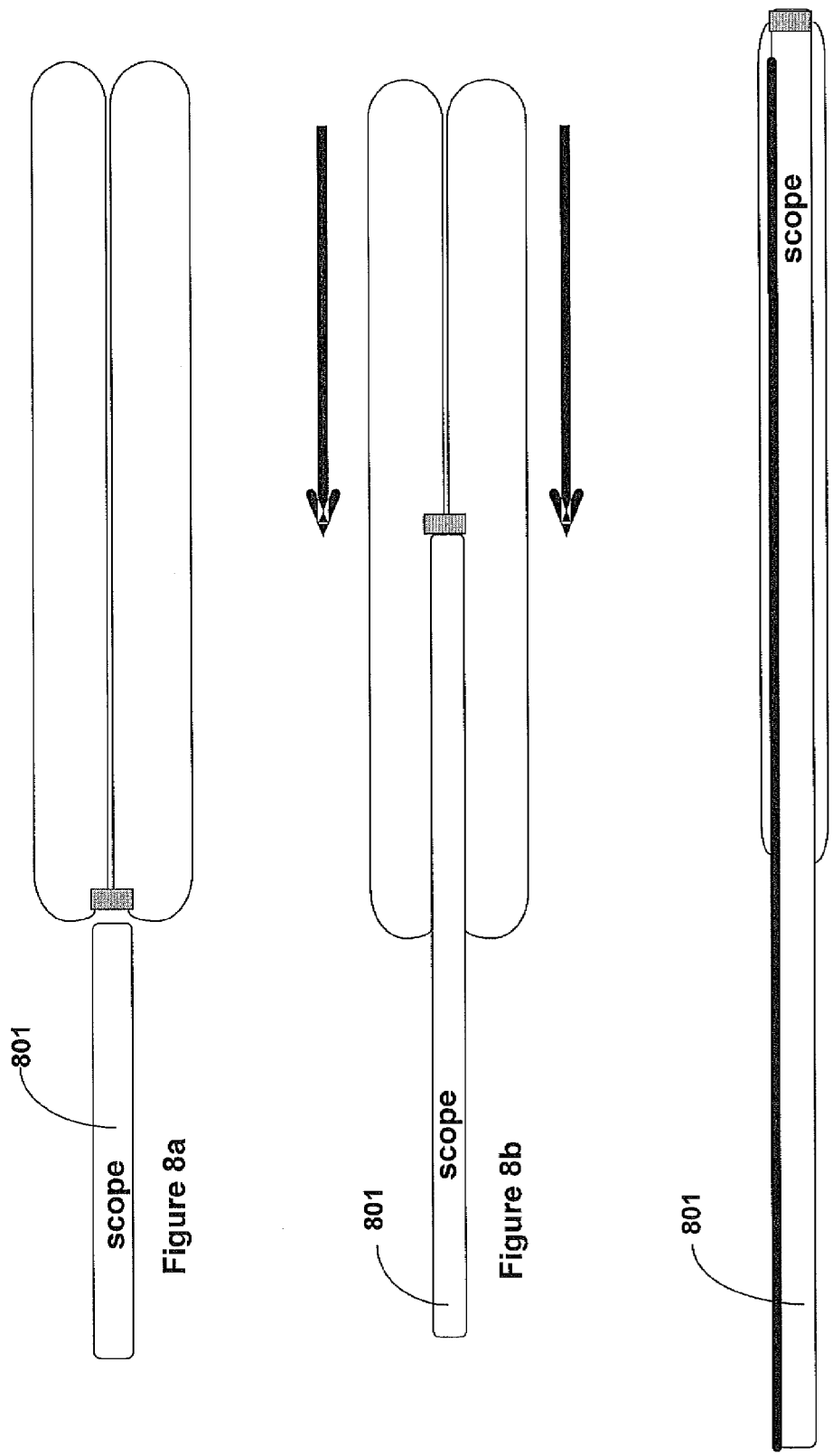

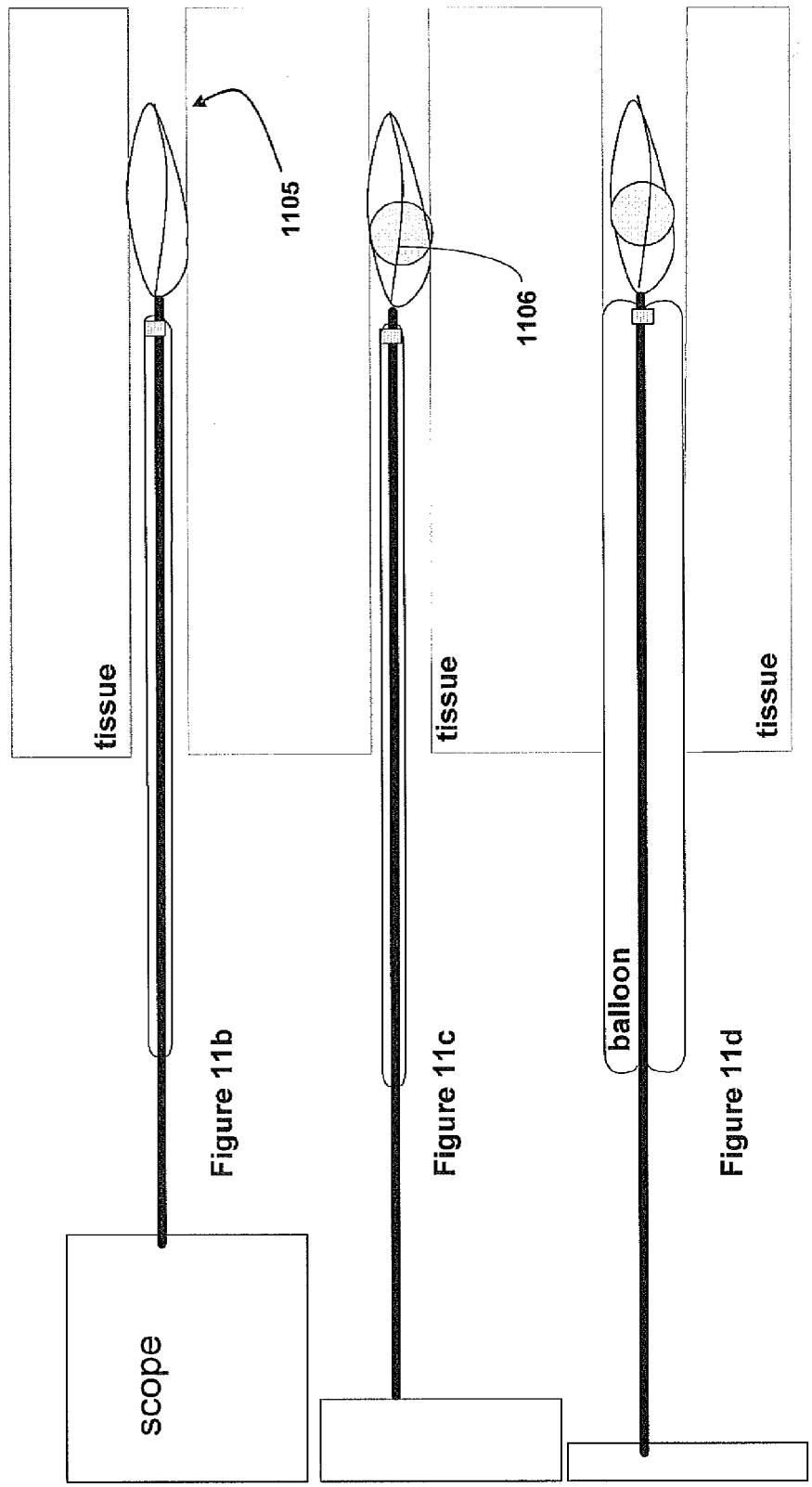

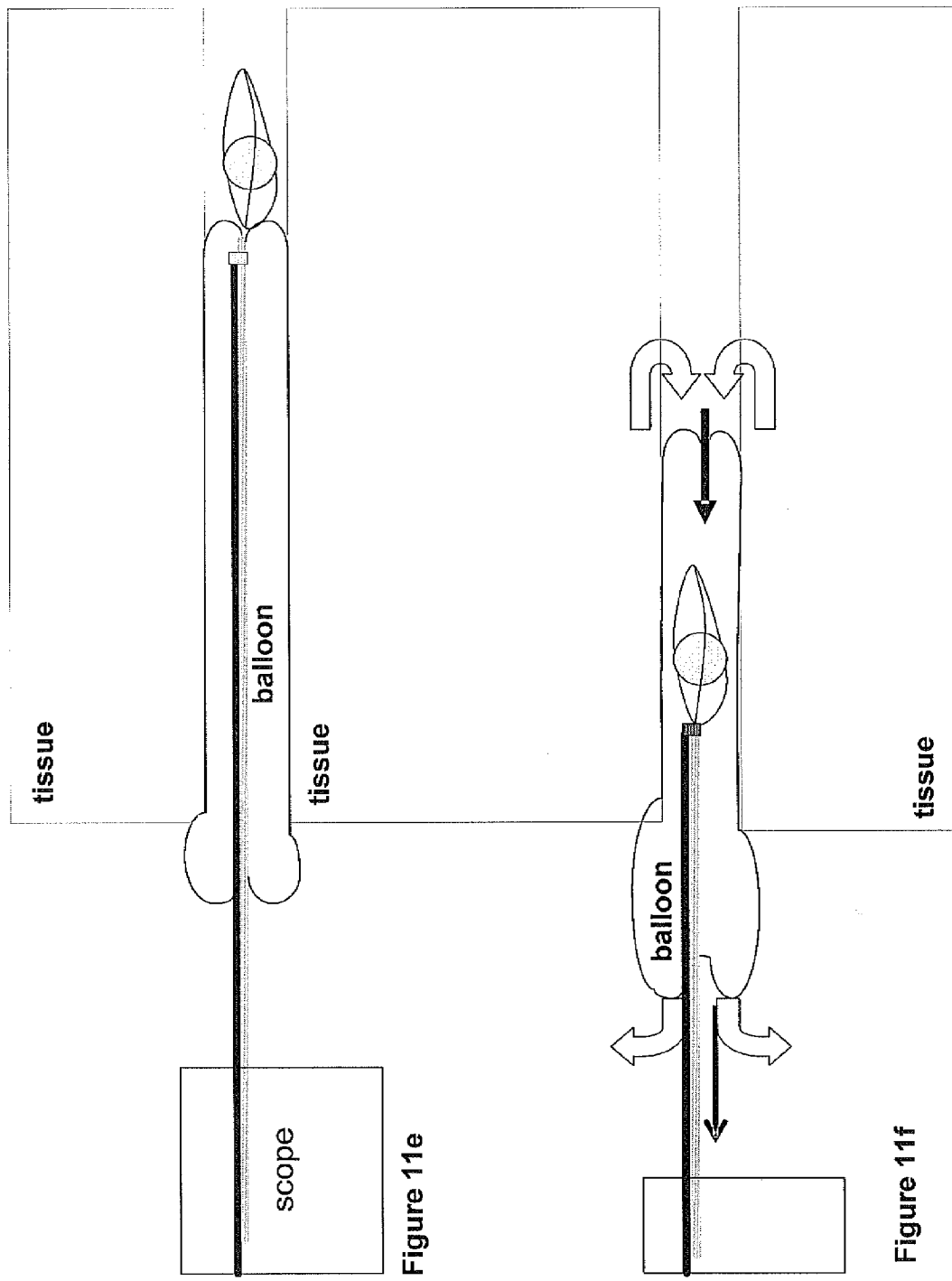

METHOD AND DEVICE FOR EXTRACTING OBJECTS FROM THE BODY

RELATED APPLICATION

This application is a continuation of U.S. application Ser. No. 11/503,617 filed Aug. 14, 2006, pending. This application additionally claims benefit to U.S. provisional application 60/708,124 filed Aug. 12, 2005, which is incorporated in its entirety herein by reference.

BACKGROUND OF THE INVENTION

1. Field of Invention

This invention relates generally to medical devices, more particularly to devices for removal of stone, foreign bodies and the like from the body.

2. Discussion of Prior Art

Existing techniques for extraction of stones from the body such as in the case of stones lodged in the urinary collecting system and in the biliary tree can be cumbersome, inefficient and risky with respect to complications. For example, the extraction of urinary stones often requires cystoscopic balloon dilation of the distal ureter using a high pressure balloon to increase the capacity of the ureter in order to allow decreased resistance with passage of the ureteroscope and extraction of the stone or its fragments. This high pressure balloon requires a costly pressure gauge and can be traumatic to the ureter placing the ureter at risk for stricture formation. After dilation, an ureteroscope is inserted and lithotripsy performed if the stone is too large for extraction. The stone is then engaged under direct vision with a basket or similar device and then withdrawn into the bladder where the stone is then considered passed. This technique requires that the stone be of sufficiently diminutive size (which is usually not the case with a lodged stone) or that the stone be fragmented with a device such as a laser which in itself carries the risk of injury to the ureter. Furthermore, extraction of a stone engaged in a wire basket carries the risk of frictional damage to the ureteral mucosa and wall, the risk of a retained basket engaged with stone requiring tertiary referral or open surgery, or the risk of catastrophic avulsion injury of the ureter.

The above time consuming, costly and risky standard techniques begs for the development of a device which will provide a less cumbersome, safer, more efficient and less costly technique to treat the extremely common problem of urinary stone disease. Other inventors have attempted to address this vexing task.

Hardwick, U.S. Pat. No. 4,469,100, proposed a device in which the stone is drawn into the balloon by intussusception, protecting the ureteral walls from the friction with stone extraction. The deficiencies of this idea include the blind passage of the device to the stone (i.e.: not under direct visualization as with the standard technique), dependence upon suction to engage a stone which has an irregular surface not amenable to suction seal for traction, and, most significantly, the device's construction where the balloon is attached to the catheter near its proximal and distal ends. The result of the latter construction is that, while the stone achieves sanctuary within the confines of the balloon's wall during intussusception, the external surface of the balloon is withdrawn in direct opposition to the ureteral wall when extracting the stone which places the ureter at risk for injury.

Another inventor who attempts to solve the existing problems with stone extraction is Drettler, U.S. Pat. No. 4,927,426. Here a catheter-like device is used which allows a laser fiber for lithotripsy but suffers the same deficiencies as Hardwick's device. U.S. Pat. Nos. 4,243,040 and 4,295,464, likewise, suffer similar problems.

Current techniques for biliary stone extraction also can be cumbersome, inefficient and risky for complication. Gallstones may become lodged in the biliary tree, often at the sphincter of Oddi which may result in biliary colic and cholangitis or pancreatitis. Many surgical devices and techniques exist for treatment of these stones confined to the biliary tree and unable to pass to the duodenum. Access to and extraction of biliary stones often require balloon dilation or sphincterotomy at the duodenal papilla which carries the risk of bleeding and perforation. The stone is then engaged with a basket, such as Cook's The Web™ Extraction Basket which risks, as with a urinary stone, injury of the biliary ductal system and retention of the basket.

Another technique for stone extraction uses a balloon such as that described by Karpeil, et al., U.S. Pat. No. 6,692,484 B1, where the sphincter is dilated and a second balloon is used to push the stone through into the duodenum. Similar balloons, such as the Cook Endoscopy Tri-Ex® Triple Lumen Extraction Balloon, often requires sphincterotomy. These balloons in general work well but do not directly control the stone as with a basket which can sometimes leave the stone wedged between the balloon and ductal wall.

Whatever the precise merits, features, and advantages of the above cited references, none of them achieves or fulfills the purposes of the present invention.

SUMMARY OF THE INVENTION

The present invention provides an apparatus used to remove a unwanted object comprising: a guide; an expandable toroidal balloon pre-rolled and only attached to a distal end of said guide's external surface and is not attached to any other point of said guide, said toroidal balloon unrolled over a length of said guide such that said toroidal balloon's surface is displaced along longitudinal length and an external surface of said guide and such that said toroidal balloon is disposed external to said guide, said expandable toroidal balloon comprising: an internal balloon surface of said toroidal balloon contacting a unwanted object; an external balloon surface of said toroidal balloon configured for contacting a biological wall; said expandable toroidal balloon draws a unwanted object via an inversion of said internal balloon surface and external balloon surface, with said inversion safely guiding removal of said unwanted object without sliding of said external balloon surface against any contacted biological wall, but by allowing low friction extraction by sliding of said internal balloon surface of said toroidal balloon.

The present invention also provides an apparatus used to remove a unwanted object comprising: guide; an expandable toroidal balloon constructed over a tube matching an external configuration of said guide's external surface, said toroidal balloon only attached to a distal end of said guide and is not attached to any other point of said guide, said tube with expandable toroidal balloon constructed over it allowing passage of said guide such that said tube with expandable toroidal balloon is disposed along external longitudinal length of said guide, said expandable toroidal balloon comprising: an internal balloon surface of said toroidal balloon contacting a unwanted object; an external balloon surface of said toroidal balloon configured for contacting a biological wall; said expandable toroidal balloon draws a unwanted object via an inversion of said internal balloon surface and external balloon surface, with said inversion safely guiding removal of said unwanted object without sliding of said external balloon surface against any contacted biological wall, but by allowing low friction extraction by sliding of said internal balloon surface of said toroidal balloon.

The present invention also provides an apparatus used to remove a unwanted object comprising: a guide; an expandable toroidal balloon inflated and only attached to a distal end of said guide's external surface and is not attached to any other point of said guide, said toroidal balloon rolled back over a length of said guide such that said toroidal balloon's surface is displaced along longitudinal length and an external surface of said guide and such that said toroidal balloon is disposed external to said guide, said expandable toroidal balloon comprising: an internal balloon surface of said toroidal balloon contacting a unwanted object; an external balloon surface of said toroidal balloon configured for contacting a biological wall; said expandable toroidal balloon draws a unwanted object via an inversion of said internal balloon surface and external balloon surface, with said inversion safely guiding removal of said unwanted object without sliding of said external balloon surface against any contacted biological wall, but by allowing low friction extraction by sliding of said internal balloon surface of said toroidal balloon.

It should be noted that although artwork and the description locate the insertion of the inflation catheter at the balloon's distal end, the inflation catheter may be inserted at the balloon's proximal end without departing from the scope of the invention.

BRIEF DESCRIPTION OF THE DRAWINGS

FIGS. 7a-c illustrate another design to apply the present invention's balloon to the end of the scope.

FIGS. 8a-c illustrate yet another design to apply the present invention's balloon to the end of the scope.

FIG. 11a-f illustrate the technique of how the present invention's device can be used as a balloon instrument.

DESCRIPTION OF THE PREFERRED EMBODIMENTS

Figure 1:
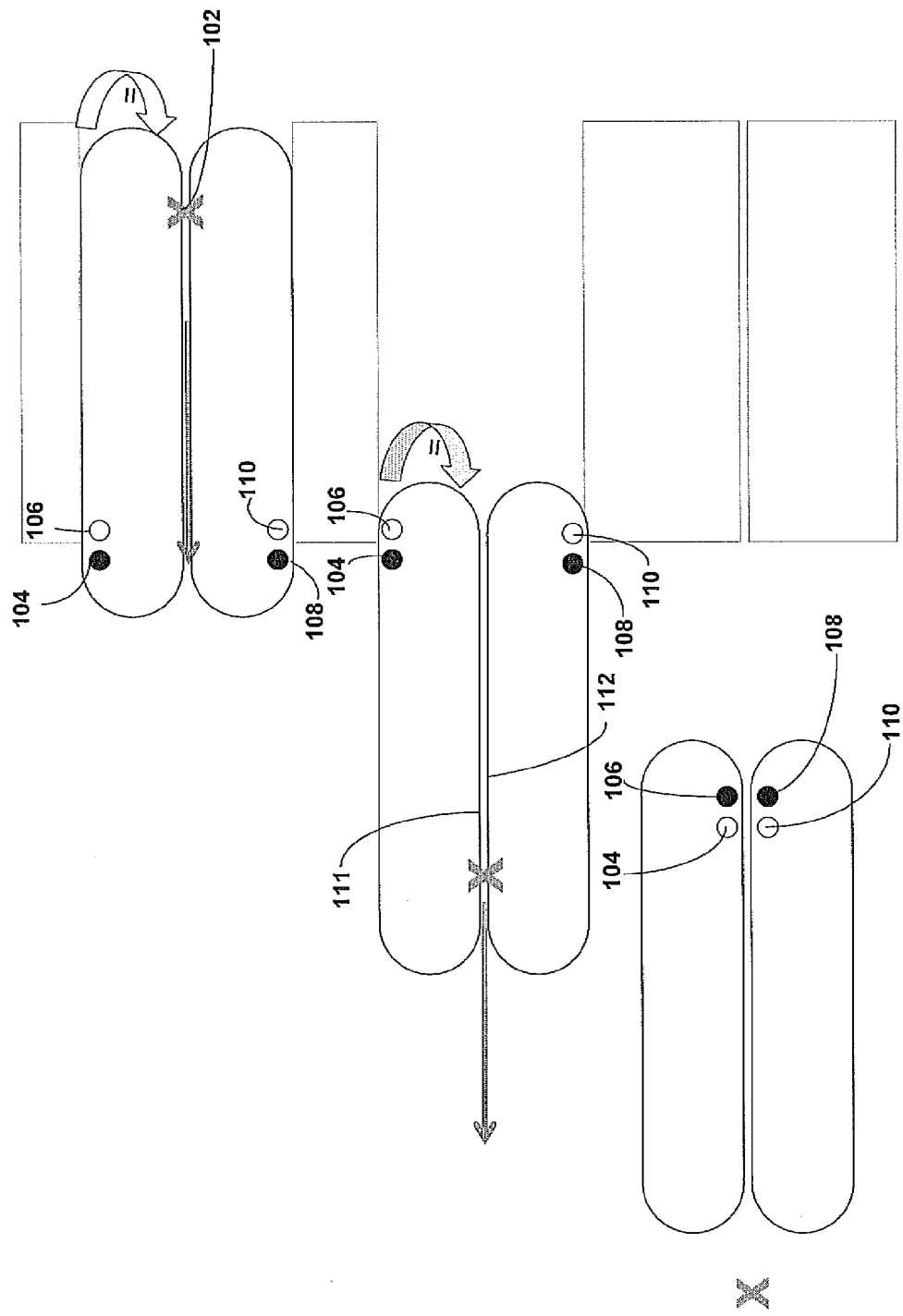
FIG. 1 illustrates an exemplary embodiment of the present invention's toroidal balloon used to remove an object that is lodged, for example, between the walls of the ureter.

While this invention is illustrated and described in a preferred embodiment, the device may be produced in many different configurations, forms and materials. There is depicted in the drawings, and will herein be described in detail, a preferred embodiment of the invention, with the understanding that the present disclosure is to be considered as an exemplification of the principles of the invention and the associated functional specifications for its construction and is not intended to limit the invention to the embodiment illustrated. Those skilled in the art will envision many other possible variations within the scope of the present invention.

The present invention provides for a toroidal balloon used in the extraction of objects from the body. FIG. 1 illustrates an exemplary embodiment of the present invention's toroidal balloon used to remove an object 102 that is lodged, for example, between the walls of the ureter. The inflated toroidal balloon is taken down internally, wherein the external balloon surface does not move relative to the ureter (i.e., there is no sliding of the external balloon surface against ureter). The inflated toroidal balloon inverts with minimal friction during extraction. Object 102 is drawn internally through the balloon. Reference points 104, 106, 108, and 110 are shown to illustrate how the balloon is taken down internally. The method illustrated in FIG. 1 teaches the low friction extraction of object 102 with the sliding of the two opposing inner balloon surfaces 111 and 112, allowing for the safe removal of a stone, surgical specimen, foreign body or organ. Inflation of balloon is preferable as it minimizes friction between the ureteroscope/basket/stone complex with extraction.

It should be noted that the only significant force with the extraction described in FIG. 1 is a radial force involved with the low friction extraction, wherein the force distribution similar to that of a wedge splitting wood. Also, since the stone itself dilates the ureter (just enough for stone passage, no more), there are no overdilation problems as with existing devices. Hence, the present invention's toroidal balloon minimizes ureteral dilation injury.

Figure 2:
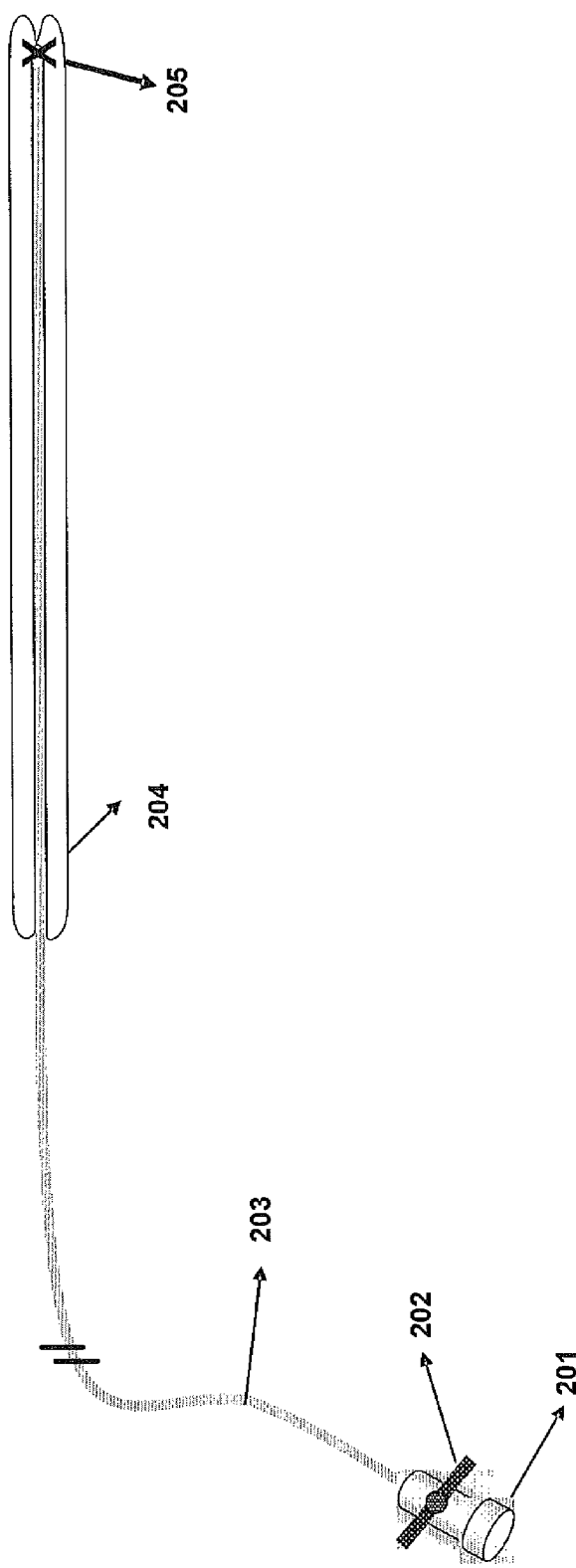
FIG. 2 illustrates one embodiment of the present invention's toroidal balloon device for attachment to a scope.

FIG. 2 illustrates one embodiment of the present invention's toroidal balloon device for attachment to a scope. The device as per the embodiment of FIG. 2 comprises luer lock connector 201, valve 202, inflation/deflation catheter 203, toroidal balloon 204, coupling attachment 205 and, optionally, a sheath 205 along catheter to guide insertion of scope.

Connector 201 is a conventional luer lock threaded to receive a conventional syringe in an air/watertight connection. It should be noted that no pressure gauge is required for a low pressure balloon for most applications. The Luer lock connection may be part of a locking valve 202 to control inflation or deflation. The valve is then connected to a catheter 203 which on the opposite end is connected with the toroidal balloon 204. The catheter 203 provides a conduit for the fluid such as saline, or a biocompatible lubricant used for inflation of the balloon. Catheter 203 is sufficient long to allow extracorporal inflation of balloon 204 (e.g., approximately 20-50 cm in length). The flexible catheter 203, constructed of polyethylene or other appropriate material, runs through the inner opening in the balloon 204, attaching at the leading end of the balloon only. Inflation/deflation catheter 203 provides a conduit for fluid such as saline or other biocompatible lubricant used for in/deflation of balloon. The proximal end of the inflation/deflation catheter 203 attaches to syringe, distal to balloon and is sufficiently long to allow extracorporal inflation (e.g., 20-50 cm in length). The inflation/deflation catheter 203 attaches at balloon's leading edge and runs internal to balloon, external to scope, and is made of polyethylene or other material. Further, the inflation/deflation catheter 203 may not be necessary with specialized endoscope (i.e., if balloon attaches directly to scope channel)

In one embodiment, the inflation/deflation catheter 203 has a non-cylindrical construction for low-profile.

Balloon 204 may be constructed of an expandable material such as latex rubber, silicone or other medical grade material/elastomer. Balloon 204 may have a lubricious coating to facilitate insertion into the ureter. Balloon 204 may be coated with a biologically active substance such as an alpha-blocker or smooth muscle relaxant. Balloon 204 may have reinforcements in the wall to maintain shape and pressure. Dilation of the ureter is only a minor role of the balloon so construction with a high tension substance may be unnecessary. A purpose of inflation is to minimize friction between the ureteroscope/basket/stone complex with extraction. Balloon 204 achieves this low friction extraction with the sliding of the two opposing inner balloon surfaces. In one non-limiting example, the length of the balloon is 2 to about 20 cm long. The length depends upon the distance from the stone to just beyond the ureteral orifice, as determined by the Urologist.

Attachment 205 of the catheter to the balloon may be of plastic or metal (alloy) and be shaped to allow simultaneous filling (or emptying) of the balloon 204 and fixation of the balloon/catheter device to the distal end of the endoscope such as a ureteroscope. Existing ureteroscopes vary in construction so the construction of the attachment will be specific to the ureteroscope. The attachment will also be formulated to allow loading of the balloon over the ureteroscope.

Attachment 205 attaches inflation/deflation catheter 203 to balloon 204 and attaches the device to a telescope. Attachment 205 facilitates loading of balloon 204 onto the telescope and facilitates insertion of the scope into ureteral orifice (e.g., may be tapered/curved at the leading edge). Attachment 205 could also helps seal the balloon closed in manufacturing process. Attachment 205, in one non-limiting example, is made using plastic or metal (alloy).

Figure 3:
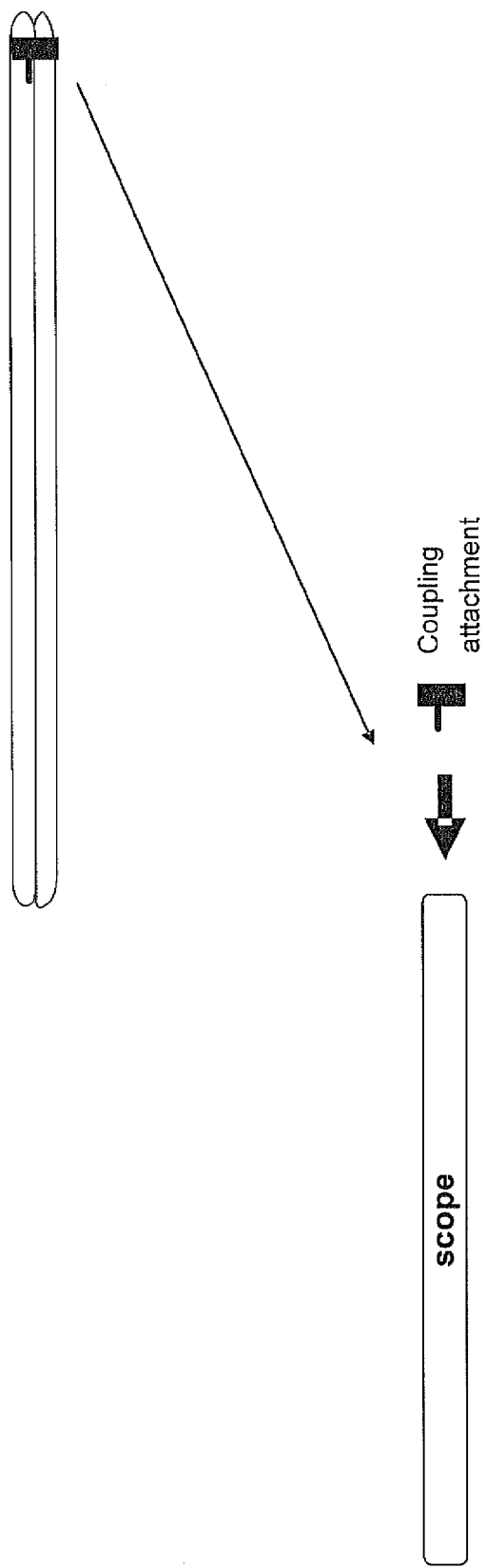
FIG. 3 illustrates such an example, wherein an attachment is configured without the inflation catheter, wherein the coupling attachment inserts directly into a channel of a scope for inflation.

Attachment 205 may be constructed for a water-tight attachment to endoscope channel for inflation. FIG. 3 illustrates such an example, wherein attachment 205 is configured without inflation catheter wherein the coupling attachment 205 inserts directly into a channel of a scope for inflation.

The toroidal balloon device may also be fashioned with dimensions and materials for other applications such as removal of gall stones, foreign bodies, surgical specimens, etc. The device is of simple construction, of low cost and disposable.

The balloon is attached to the extraction device at just one level at the distal aspect, so the stone can both be drawn via intussusception into the protective confines of the inner surface and also drawn out the entire length of the balloon and out of the patient via intussusception. The device in Hardwick's patent (U.S. Pat. No. 4,469,100) intussuscepts slightly to cover the stone but is not a toroidal balloon since it is attached both distally and proximally. Hardwick's double attachment may allow minimal inversion of the balloon to cover the stone before the balloon is pulled out, but intussusception of the balloon is not the mechanism by which a stone is extracted. The ability to invert our entire balloon is the important and unique benefit of our device.

During stone extraction using Hardwick's doubly attached balloon, after a short length of intussusception, the outer surface of his balloon must be dragged across the surface of the ureter during extraction. It seems doubtful that the friction and other physical forces would allow extraction of an inflated balloon through a tight tube such as the ureter. There is no balloon in common use which is withdrawn in the ureter while inflated and entirely by intussusception.

The present invention's balloon 204 is taken down internally with minimal friction. By contrast, Hardwick's balloon is extracted by sliding the external balloon wall against the ureteral wall. In our balloon, the only walls that slide against each other are the two internal surfaces of the balloon, wetted by the fluid used to inflate the balloon. Unlike Hardwick's balloon, the outside wall of our balloon remains stationary with respect to the ureteral wall until it inverts during the extraction.

Another important difference is that the present invention's balloon facilitates existing techniques for stone extraction. The present invention's device is added external to the ureteroscope without affecting existing techniques for stone manipulation and adds safety and efficiency to the process of stone extraction. Ureteral stones are addressed, fragmented if necessary and engaged per routine with existing devices (ureteroscopes, laser fibers and wire baskets, respectively). Urologists won't need to learn a new technique for stone manipulation. They'll need only to inflate the sleeve (balloon) for extraction. Hardwick device's, in contrast to our balloon, replaces the ureteroscope and depends upon suction to grasp the stone. This requires blind passage of the device, not under safe direct visualization as with ours, to the level of the stone, which would be difficult and risky. The ability to grasp a jagged stone by suction is suspect. In addition, suction would engage the ureteral wall.

Figure 4:
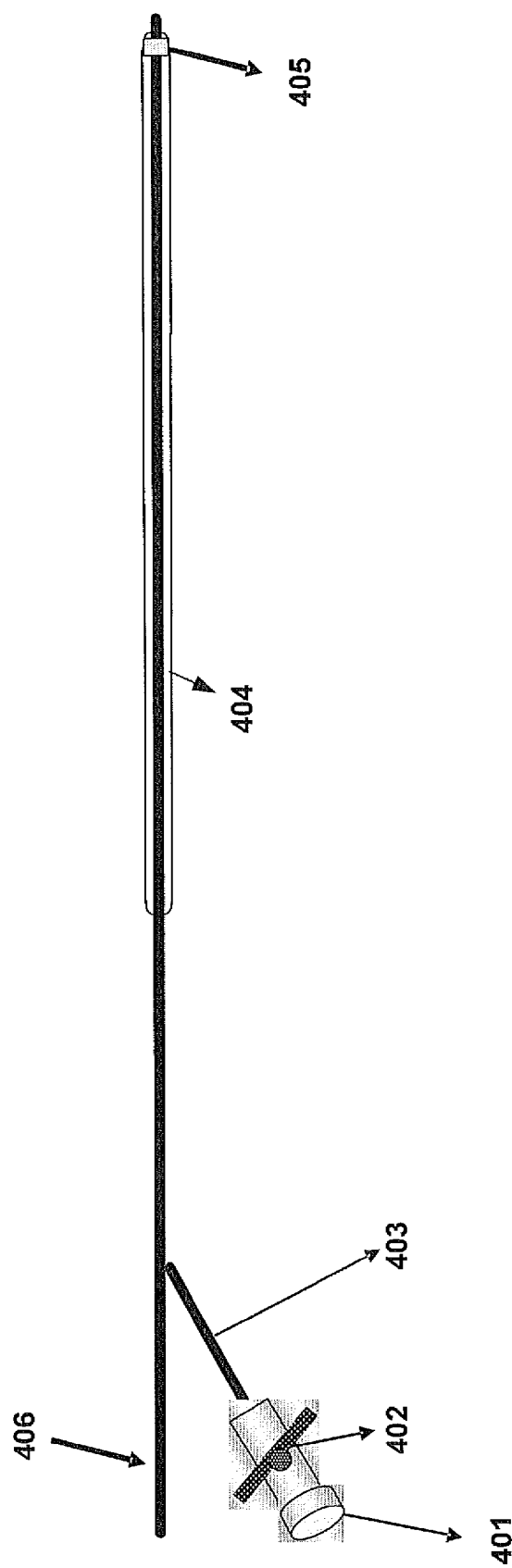
FIG. 4 illustrates another embodiment wherein the present invention's toroidal balloon comprises a luer lock connector, valve, an inflation/deflation port, a toroidal balloon, a coupling attachment to the catheter, and a catheter containing wire to open a basket.
Figure 5:
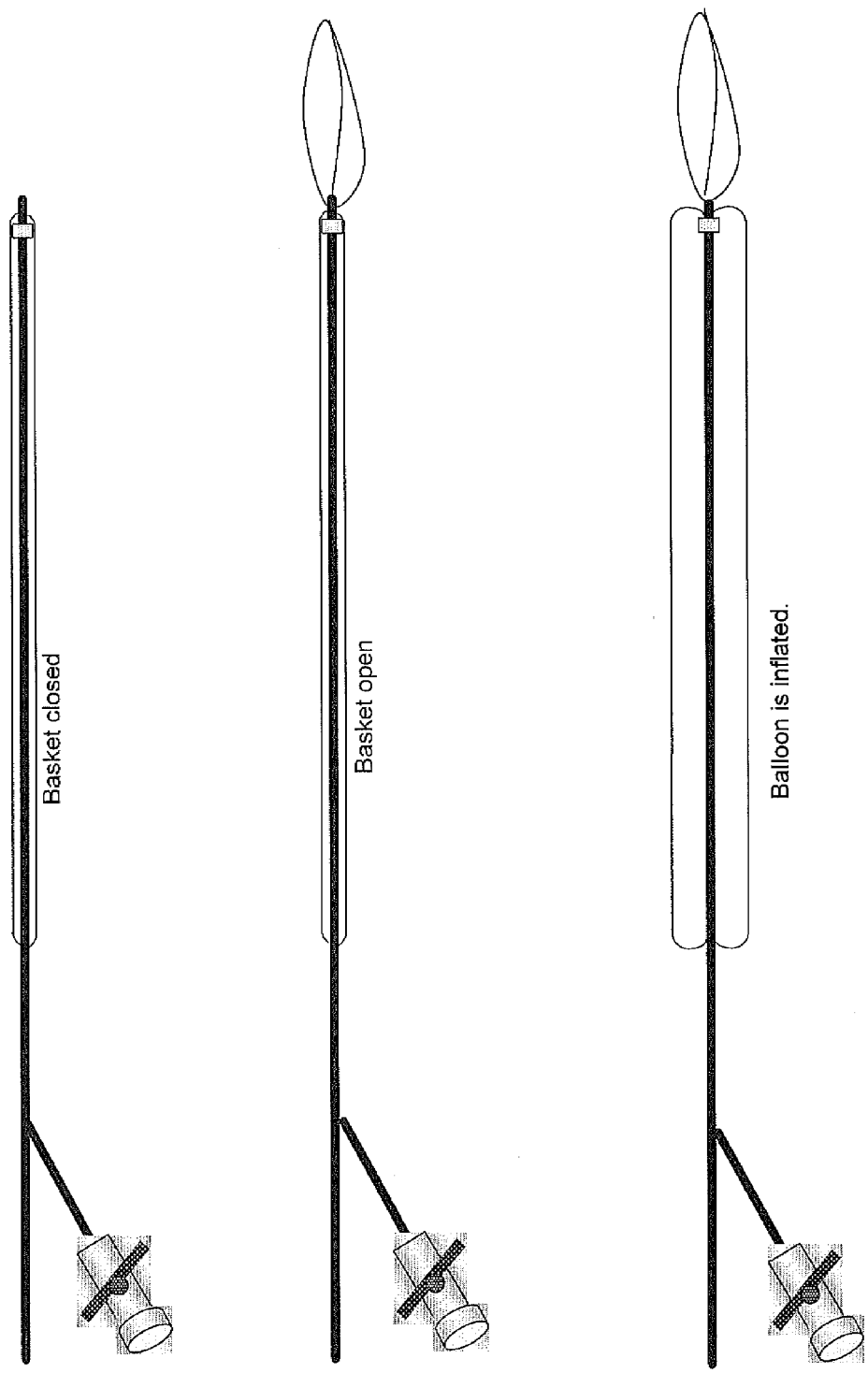
FIG. 5 illustrates scenarios wherein the basket is closed, open, and open with balloon being inflated.

FIG. 4 illustrates another embodiment wherein the present invention's toroidal balloon is used as an instrument, wherein the setup comprises a luer lock connector 401, valve 402, inflation/deflation port 403, toroidal balloon 404, coupling attachment to the catheter 405, and catheter containing wire to open basket 406. The principle of functionality is similar to that of what is outlined in FIG. 1. FIG. 5 illustrates scenarios wherein the basket is closed, open, and open with balloon being inflated.

Figure 6:
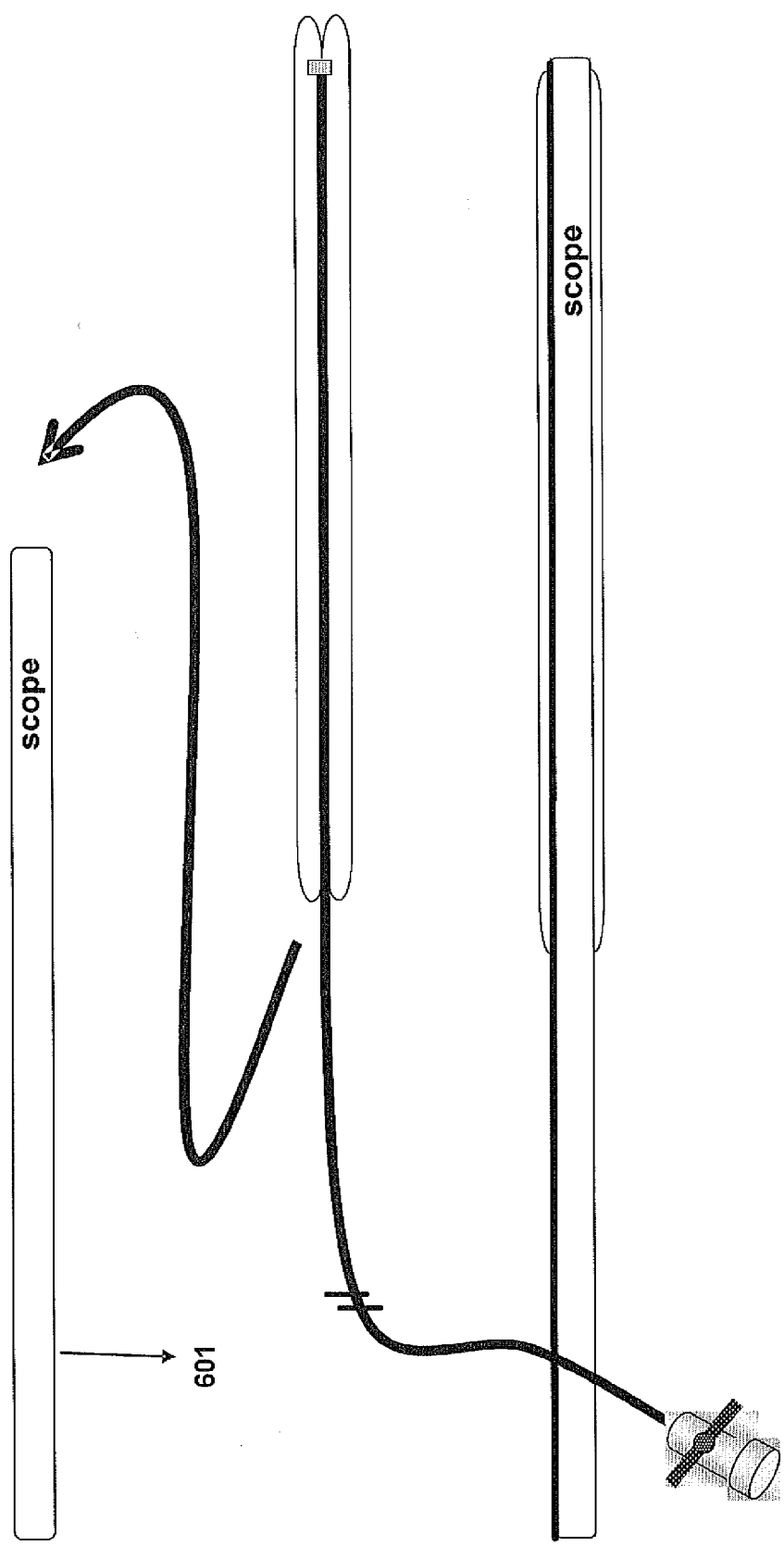
FIG. 6 illustrates a first design to apply the present invention's balloon to the end of the scope.

FIG. 6 illustrates a first design to apply the present invention's balloon to the end of the scope. In this example, the balloon is constructed over a tube matching the external conformation of the scope 601. The length of the balloon is at least the distance from the stone to uretral orifice.

FIGS. 7a-c illustrate another design to apply the present invention's balloon to the end of the scope. As shown in FIG. 7a, the balloon is pre-rolled and attached to the end of the scope 701 and, as shown in FIGS. 7b-c, the pre-rolled balloon is then unrolled, like a condom, onto the telescope. As mentioned previously, the length of the balloon is at least the distance from the stone to uretral orifice.

FIGS. 8a-c illustrate yet another design to apply the present invention's balloon to the end of the scope. As shown in FIG. 8a, the balloon is inflated before application to the scope 801. As shown in FIG. 8b, the inflated balloon is attached to the end of the scope 801 and, then, rolled back over the scope 801. As shown in FIG. 8c, the balloon is then deflated and is ready for insertion into the patient.

Figure 9A:
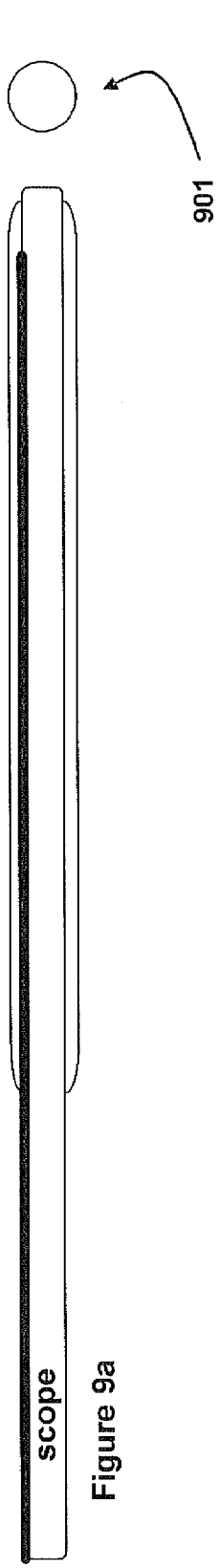
FIGS. 9a-9c illustrate the present invention's balloon having the scope being advanced to the stone, the stone being fragmented and engaged with a basket, and the balloon being inflated, respectively.
Figure 9B:
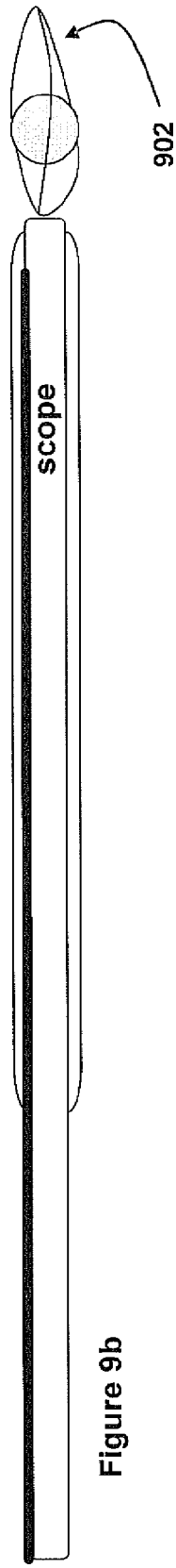
Figure 9C:
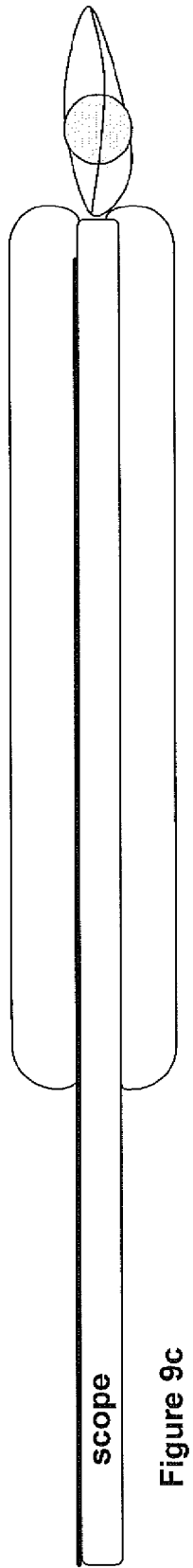
Figure 10:
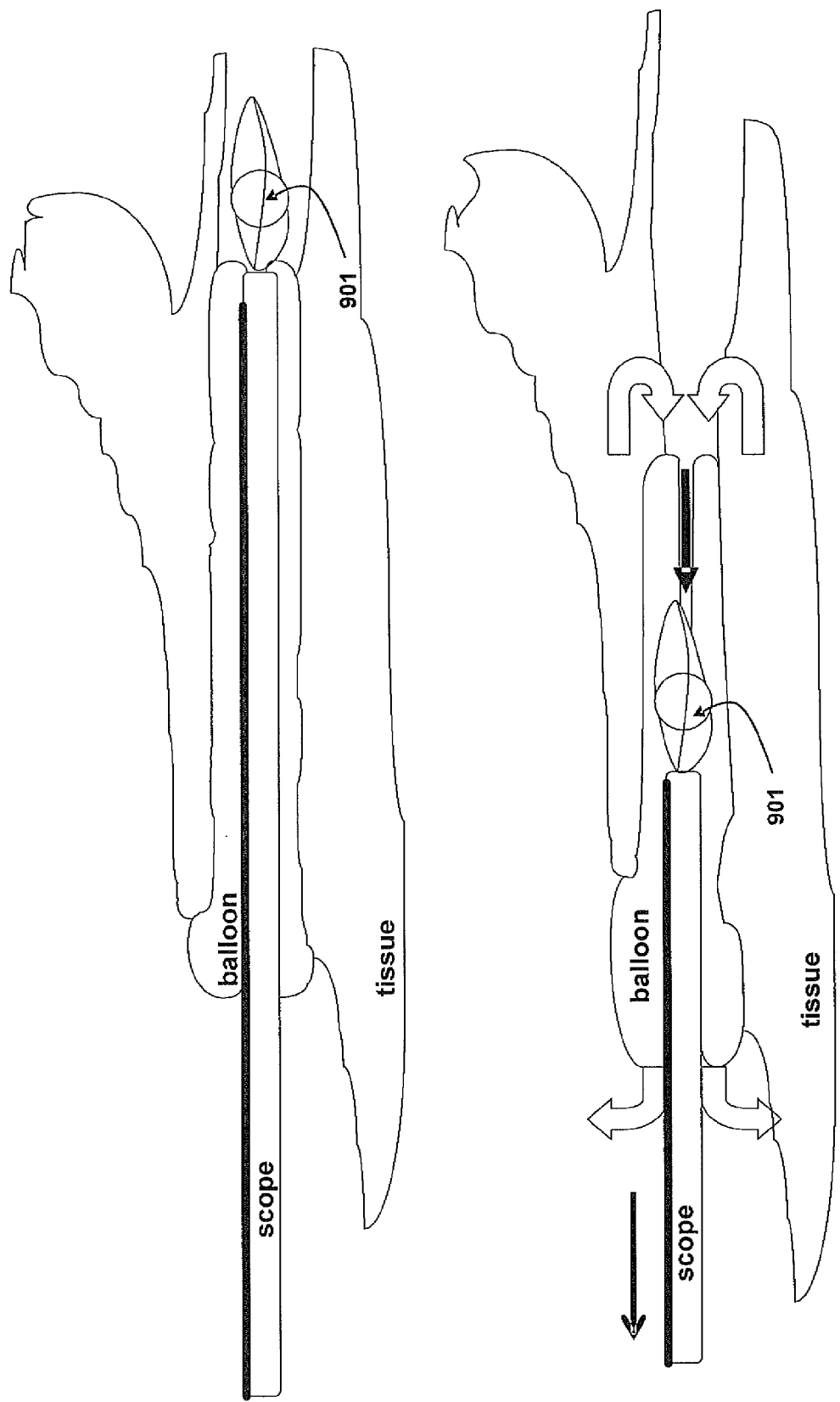
FIG. 10 illustrates how the stone is withdrawn with minimal friction based on the teaching of the present invention as illustrated and described according to FIG. 1.

FIG. 9a illustrates the present invention's balloon having the scope being advanced to stone 901. The stone is then fragmented with a laser, if necessary, and is engaged within basket 902 as shown in FIG. 9b. In FIG. 9c, the toroidal balloon is then inflated. FIG. 10 illustrates how the stone 901 is withdrawn with minimal friction based on the teaching of the present invention as illustrated and described according to FIG. 1.

FIGS. 11a-f illustrate the technique of how the present invention's device can be used as a balloon instrument. According to FIG. 11a, basket device 1102 with balloon component 1104 of the basket device 1102 are inserted into the scope. According to FIG. 11b, the basket device 1102 is advanced into the duct and the basket 1105 is opened. According to FIG. 11c, the stone 1106 is engaged in basket 1105.

Next, as shown in FIG. 11d, the balloon is inflated. FIG. 11e depicts an example wherein the balloon is inflated within the duct with the stone engaged in the basket. FIG. 11f illustrates how the stone is withdrawn with minimal friction based on the teaching of the present invention as illustrated and described according to FIG. 1.

The present invention can be used in the extraction of various objects, including, but not limited to: percutaneous stone extraction (PCNL), bladder stones, urethral stones, tracheal foreign bodies, rectal foreign bodies, surgical specimens, endotracheal tubes, or virtually in any endoscopic procedure.

Therefore, the present invention provides a toroidal balloon of a simple construction and has a low-cost of manufacturing. Further, the present invention's toroidal balloon provides for a low risk of device failure. The present invention's device may be a disposable toroidal balloon. The present invention's device may also be fashioned with dimensions and materials for other applications such as removal of gall stones, foreign bodies, surgical specimens, etc.

The present invention allows for the development of specialized ureteroscopes, such as a smaller scope with a balloon attachment for stone basketing and extraction only. Further, the present invention's toroidal balloon is applicable to multiple medical and veterinary specialties and body systems.

Although the examples of the specification detail the extraction of a foreign object, it should be noted that the toroidal balloon of the present invention can also be utilized for the low friction insertion of a foreign object.

In such a scenario, the present invention's expandable toroidal balloon used to insert a foreign object comprises: an internal balloon surface contacting a foreign object and an external balloon surface contacting a biological wall, wherein the foreign object is drawn externally through the expandable toroidal balloon via an inversion of the internal balloon surface and external balloon surface. The inversion safely guides the insertion of the foreign object (into, for example, the tract) without sliding of the external balloon surface against said biological wall.

In this scenario, the method to insert a foreign object comprises: (a) inflating a toroidal balloon having an internal balloon surface and an external balloon surface; (b) inserting a foreign object in said toroidal balloon, wherein the foreign object contacts the internal balloon surface; (c) inserting the toroidal balloon into a tract wherein the external balloon surface contacts a biological wall of said tract; and (d) inverting the internal balloon surface and external balloon surface to move the foreign object externally through the expandable toroidal balloon, wherein the inversion safely guides the insertion of the foreign object in the tract without sliding of the external balloon surface against the biological wall.

It should additionally be noted that the present invention's balloon, in an extended embodiment, serves as a tissue dissector.

CONCLUSION

A system and method has been shown in the above embodiments for the effective implementation of a method and device for extracting/inserting objects from the body. While various preferred embodiments have been shown and described, it will be understood that there is no intent to limit the invention by such disclosure, but rather, it is intended to cover all modifications and alternate constructions falling within the spirit and scope of the invention, as defined in the appended claims. For example, the present invention should not be limited by size, materials, or specific manufacturing techniques.

The invention claimed is:

1. An apparatus used to remove a unwanted object comprising:
   a guide;
   an expandable toroidal balloon pre-rolled and only attached to a distal end of said guide's external surface and is not attached to any other point of said guide, said toroidal balloon unrolled over a length of said guide such that said toroidal balloon's surface is displaced along longitudinal length and an external surface of said guide and such that said toroidal balloon is disposed external to said guide, said expandable toroidal balloon comprising:
   an internal balloon surface of said toroidal balloon contacting a unwanted object;
   an external balloon surface of said toroidal balloon configured for contacting a biological wall;
   said expandable toroidal balloon draws a unwanted object via an inversion of said internal balloon surface and external balloon surface, with said inversion safely guiding removal of said unwanted object without sliding of said external balloon surface against any contacted biological wall, but by allowing low friction extraction by sliding of said internal balloon surface of said toroidal balloon.

2. An expandable toroidal balloon as per claim 1, wherein said toroidal balloon is externally attached to a scope.

3. An expandable toroidal balloon as per claim 1, wherein said toroidal balloon is externally attached to a medical balloon instrument.

4. An expandable toroidal balloon as per claim 1, wherein said balloon is made of any of the following materials: latex rubber, silicone, or elastomer.

5. An expandable toroidal balloon as per claim 1, wherein said unwanted object is any of the following: percutaneous stone, bladder stone, urethral stone, tracheal unwanted body, rectal unwanted body, surgical specimen, or endotracheal tubes.

6. The apparatus of claim 1, wherein said guide is an ureteroscope.

7. An apparatus used to remove a unwanted object comprising:
   a guide;
   an expandable toroidal balloon constructed over a tube matching an external configuration of said guide's external surface, said toroidal balloon only attached to a distal end of said guide and is not attached to any other point of said guide, said tube with expandable toroidal balloon constructed over it allowing passage of said guide such that said tube with expandable toroidal balloon is disposed along external longitudinal length of said guide, said expandable toroidal balloon comprising:
   an internal balloon surface of said toroidal balloon contacting a unwanted object;
   an external balloon surface of said toroidal balloon configured for contacting a biological wall;
   said expandable toroidal balloon draws a unwanted object via an inversion of said internal balloon surface and external balloon surface, with said inversion safely guiding removal of said unwanted object without sliding of said external balloon surface against any contacted biological wall, but by allowing low friction extraction by sliding of said internal balloon surface of said toroidal balloon.

8. The apparatus of claim 7, wherein said balloon is made of any of the following materials: latex rubber, silicone, or elastomer.

9. The apparatus of claim 7, wherein said unwanted object is any of the following: percutaneous stone, bladder stone, urethral stone, tracheal unwanted body, rectal unwanted body, surgical specimen, or endotracheal tubes.

10. The apparatus of claim 7, wherein said guide is ureteroscope.

11. An apparatus used to remove a unwanted object comprising:
a guide;
an expandable toroidal balloon inflated and only attached to a distal end of said guide's external surface and is not attached to any other point of said guide, said toroidal balloon rolled back over a length of said guide such that said toroidal balloon's surface is displaced along longitudinal length and an external surface of said guide and such that said toroidal balloon is disposed external to said guide, said expandable toroidal balloon comprising:
an internal balloon surface of said toroidal balloon contacting a unwanted object;
an external balloon surface of said toroidal balloon configured for contacting a biological wall;
said expandable toroidal balloon draws a unwanted object via an inversion of said internal balloon surface and external balloon surface, with said inversion safely guiding removal of said unwanted object without sliding of said external balloon surface against any contacted biological wall, but by allowing low friction extraction by sliding of said internal balloon surface of said toroidal balloon.

12. The apparatus of claim 11, wherein said guide is any of the following: endoscope or ureteroscope.

13. The apparatus of claim 11, wherein said balloon is made of any of the following materials: latex rubber, silicone, or elastomer.

14. The apparatus of claim 11, wherein said foreign object is any of the following: percutaneous stone, bladder stone, urethral stone, tracheal foreign body, rectal foreign body, surgical specimen, or endotracheal tubes.

* * * * *